(12) United States Patent
Hong

(10) Patent No.: US 8,579,438 B2
(45) Date of Patent: Nov. 12, 2013

(54) APPARATUS AND METHOD FOR DIAGNOSING DISEASE INVOLVING OPTIC NERVE

(75) Inventor: Seung Woo Hong, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 286 days.

(21) Appl. No.: 12/905,681

(22) Filed: Oct. 15, 2010

(65) Prior Publication Data

US 2011/0279775 A1    Nov. 17, 2011

(30) Foreign Application Priority Data

May 14, 2010    (KR) .......................... 10-2010-0045559

(51) Int. Cl.
   *A61B 3/14*    (2006.01)
(52) U.S. Cl.
   USPC .......................................... 351/206; 351/210
(58) Field of Classification Search
   USPC ................................................. 351/206, 210
   See application file for complete search history.

(56) References Cited

U.S. PATENT DOCUMENTS

| | | | |
|---|---|---|---|
| 2009/0292384 A1* | 11/2009 | Hanawa et al. | 700/104 |
| 2011/0063573 A1* | 3/2011 | Meyer et al. | 351/246 |
| 2012/0150029 A1* | 6/2012 | Debuc | 600/425 |

FOREIGN PATENT DOCUMENTS

| | | |
|---|---|---|
| JP | 2004-502483 | 1/2004 |
| JP | 2008-237839 | 10/2008 |
| WO | WO 02/03852 | 1/2002 |

\* cited by examiner

*Primary Examiner* — Mahidere Sahle
(74) *Attorney, Agent, or Firm* — Joseph Hyosuk Kim; JHK Law

(57) ABSTRACT

An apparatus and a method for diagnosing optic neuropathic diseases including glaucoma, are provided. The apparatus for diagnosing optical neuropathic diseases measures a thickness of a retinal nerve fiber layer (RNFL) using methods such as optical coherence tomography (OCT) and scanning laser polarimetry, and includes a scanning unit which scans along an optic nerve margin in the proximity of an optic nerve head, a pattern analyzing unit which analyzes a pattern of the RNFL scanned by the scanning unit, and a disease determining unit which determines a presence of the disease based on the pattern of the RNFL analyzed by the pattern analyzing unit.

6 Claims, 4 Drawing Sheets

APPARATUS AND METHOD FOR DIAGNOSING DISEASE INVOLVING OPTIC NERVE

CROSS-REFERENCE TO RELATED APPLICATIONS

This application claims priority from Korean Patent Application No. 10-2010-0045559, filed on 14 May 2010, in the Korean Intellectual Property Office, the disclosure of which is incorporated herein by reference in its entirety.

BACKGROUND OF THE INVENTION

1. Field of the Invention

Apparatuses and methods consistent with the disclosure provided herein relate to diagnosing diseases such as glaucoma which damage optic nerve, and more particularly, to an apparatus and a method for diagnosing diseases associated with optic nerve by measuring a thickness of retinal nerve fiber layer (RNFL) using methods including optical coherence tomography (OCT) or scanning laser polarimetry (SLP).

2. Description of the Related Art

Among many eye diseases that affect optic nerve, glaucoma is a group of eye diseases that damages the optic nerve and impairs the vision field in a characteristic pattern due to risk factors such as elevated intraocular pressure. Glaucoma leaves permanent loss of visual field to a patient unless diagnosed and treated properly at the early stage. Therefore, it is very important to detect several variants associated with glaucoma and attend to them early on. It is important to do so especially for the case of glaucoma, since glaucoma sometimes does not develop the elevated intraocular pressure (that is, intraocular pressure sometimes remains in normal range) or other eye problems and so is left undiagnosed and untreated.

There are many tests including ophthalmoscopy, stereography or perimetry conducted to detect glaucoma in the early stage. However, the drawback of inspecting optic nerve by the ophthalmoscopy and stereography is that it is difficult to detect the minute changes in the early stage and the evaluation is subjective. The perimetry is relatively more objective inspection than the above-mentioned tests, but considering the study results which indicate that the perimetry is not able to detect the abnormality until approximately 40% of damages are done to the retinal ganglion cells, the perimetry has a limit as a method to diagnose early-stage of glaucoma.

Accordingly, many tests have been suggested for early diagnosis of glaucoma, and these tests focus more on the glaucomatous changes which occur before the abnormality becomes detectable by the perimetry.

Among various changes associated with glaucoma, it has been reported that the change in the retinal nerve fiber layer (RNFL) precedes the change in the optic disk and vision field. Accordingly, it has been suggested that it would be efficient to inspect the RNFL for the early diagnosis of glaucoma.

Various equipments have been developed to be used to detect the changes in the RNFL. Among these, the optical coherence tomography (OCT) and the scanning laser polarimetry quantitate the thickness of the RNFL based on the reflection from a border between retina and vitreous to measure the thickness of four peripapillary sectors in upper, lower, nose and ear directions, the thickness of the twelve clock-hour sectors, and the average of all the obtained thickness. Many studies suggest that the OCT and the scanning laser polarimetry are useful methods to diagnose glaucoma in the early stage, since the OCT images help to detect a change of the RNFL which becomes thinner at a location where the visual field defect develops.

Generally, glaucoma is diagnosed using OCT and scanning laser polarimetry based on a comparison between the thickness of the RNFL as measured and the thickness of a normal healthy subject. However, considering the fact that even healthy RNFLs without glaucoma vary in the thickness depending on persons, and the average thickness of the healthy RNFL varies depending on areas, the sensitivity and specificity have yet to be improved particularly in relation to early diagnosis of glaucoma.

SUMMARY OF THE INVENTION

Exemplary embodiments of the present inventive concept overcome the above disadvantages and other disadvantages not described above. Also, the present inventive concept is not required to overcome the disadvantages described above, and an exemplary embodiment of the present inventive concept may not overcome any of the problems described above.

According to one embodiment, an apparatus and a method for diagnosing glaucoma are provided, which are capable of improving performance of early diagnosis of glaucoma by improving sensitivity and specificity of diagnosis of glaucoma.

In one embodiment, an apparatus for diagnosing optic neuropathic diseases including glaucoma, by measuring a thickness of a retinal nerve fiber layer (RNFL), may include a scanning unit which scans along an optic nerve margin in the proximity of an optic nerve head, a pattern analyzing unit which analyzes a pattern of the RNFL scanned by the scanning unit, and a disease determining unit which determines a presence of the disease based on the pattern of the RNFL analyzed by the pattern analyzing unit.

The scanning unit may preferably scan along the optic nerve margin in the proximity of the optic nerve head, in a circular fashion.

The pattern analyzing unit may compute a regression equation based on the pattern of the scanned RNFL.

The disease determining unit may determine the presence of the disease, if a difference between an estimate and an actual measurement based on the regression equation computed by the pattern analyzing unit exceeds a preset range.

The pattern analyzing unit may compute the regression equation based on locations and thicknesses of a first peak and a second peak of a superior region of the optic nerve head, and locations and thickness of toughs appearing between the first and second peaks.

The pattern analyzing unit may compute the regression equation based on locations and thicknesses of a second peak and a third peak of a superior region of the optic nerve head, and locations and thickness of toughs appearing between the second and third peaks.

The pattern analyzing unit may compute the regression equation based on locations and thicknesses of a first peak and a second peak of an inferior region of the optic nerve head, and locations and thickness of toughs appearing between the first and second peaks.

The pattern analyzing unit may compute the regression equation based on locations and thicknesses of a second peak and a third peak of an inferior region of the optic nerve head, and locations and thickness of toughs appearing between the second and third peaks.

The pattern analyzing unit may compute the regression equation based on locations and thicknesses of first peaks of a superior region and an inferior region of the optic nerve head, and locations and thickness of toughs appearing between the first peaks.

In another embodiment, a method for diagnosing optic neuropathic diseases including glaucoma, using methods such as optical coherence tomography (OCT) and laser scanning laser polarimetry, may include scanning along an optic nerve margin in the proximity of an optic nerve head, analyzing a pattern of a retinal nerve fiber layer (RNFL) scanned by the scanning, and determining a presence or an absence of the disease based on the pattern of the RNFL analyzed by the analyzing.

The scanning may include scanning along the optic nerve margin in the proximity of the optic nerve head, in a circular fashion.

The analyzing may include computing a regression equation based on the pattern of the scanned RNFL.

The determining may include determining the presence of the disease, if a difference between an estimate and an actual measurement based on the regression equation computed by the pattern analyzing unit exceeds a preset range.

The analyzing may include computing the regression equation based on locations and thicknesses of a first peak and a second peak of a superior region of the optic nerve head, and locations and thickness of toughs appearing between the first and second peaks.

The analyzing may include computing the regression equation based on locations and thicknesses of a second peak and a third peak of a superior region of the optic nerve head, and locations and thickness of toughs appearing between the second and third peaks.

The analyzing may include computing the regression equation based on locations and thicknesses of a first peak and a second peak of an inferior region of the optic nerve head, and locations and thickness of toughs appearing between the first and second peaks.

The analyzing may include computing the regression equation based on locations and thicknesses of a second peak and a third peak of an inferior region of the optic nerve head, and locations and thickness of toughs appearing between the second and third peaks.

The analyzing may include computing the regression equation based on locations and thicknesses of first peaks of a superior region and an inferior region of the optic nerve head, and locations and thickness of toughs appearing between the first peaks.

According to the embodiments, since the optic neuropathic diseases are diagnosed by measuring a thickness of the retinal nerve fiber layer (RNFL) using the optical coherence tomography (OCT), scanning laser polarimetry, or the like, improved sensitivity and specificity of diagnosis to diseases such as glaucoma which affect optic nerve is provided.

BRIEF DESCRIPTION OF THE DRAWINGS

The above and/or other aspects of the present inventive concept will be more apparent by describing certain exemplary embodiments of the present inventive concept with reference to the accompanying drawings, in which.

DETAILED DESCRIPTION OF EXEMPLARY EMBODIMENTS

Figure 1:
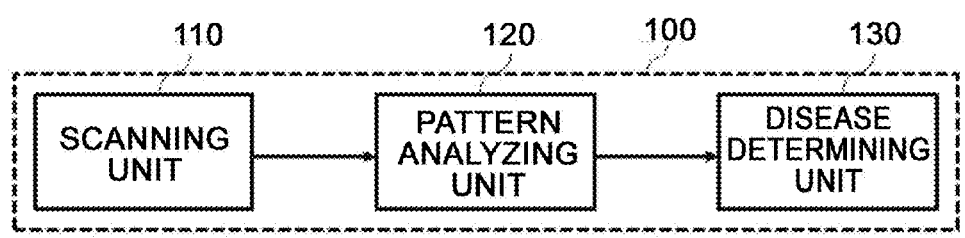
FIG. 1 is a schematic block diagram of an apparatus for diagnosing optic neuropathic diseases according to an embodiment.

Certain exemplary embodiments of the present inventive concept will now be described in greater detail with reference to the accompanying drawings.

In the following description, same drawing reference numerals are used for the same elements even in different drawings. The matters defined in the description, such as detailed construction and elements, are provided to assist in a comprehensive understanding of the present inventive concept. Accordingly, it is apparent that the exemplary embodiments of the present inventive concept can be carried out without those specifically defined matters.

Also, well-known functions or constructions are not described in detail since they would obscure the invention with unnecessary detail.

Furthermore, in explaining the elements according to an embodiment, terms may be added by 'first', 'second', 'A', '(a)', or '(b)'. However, these modifying terms are used only to distinguish specific elements from others and should not be construed as limiting essence, order or sequence of the specific elements. Furthermore, when a specific element is described as being 'linked', 'coupled' or 'connected' to another element, it should be understood that the specific element may be linked or connected to another element directly, or via yet another element which may be 'linked', 'coupled' or 'connected' between the specific element and another element.

FIG. 1 is a schematic block diagram of an apparatus for diagnosing optic neuropathic diseases (shortly, 'diagnosing apparatus') according to an embodiment. The diagnosing apparatus 400 may measure the thickness of the RNFL using optical coherence tomography (OCT) and scanning laser polarimetry. Referring to FIG. 1, the diagnosing apparatus 100 according to one embodiment may include a scanning unit 110, a pattern analyzing unit 120, and a disease determining unit 130.

Figure 2:
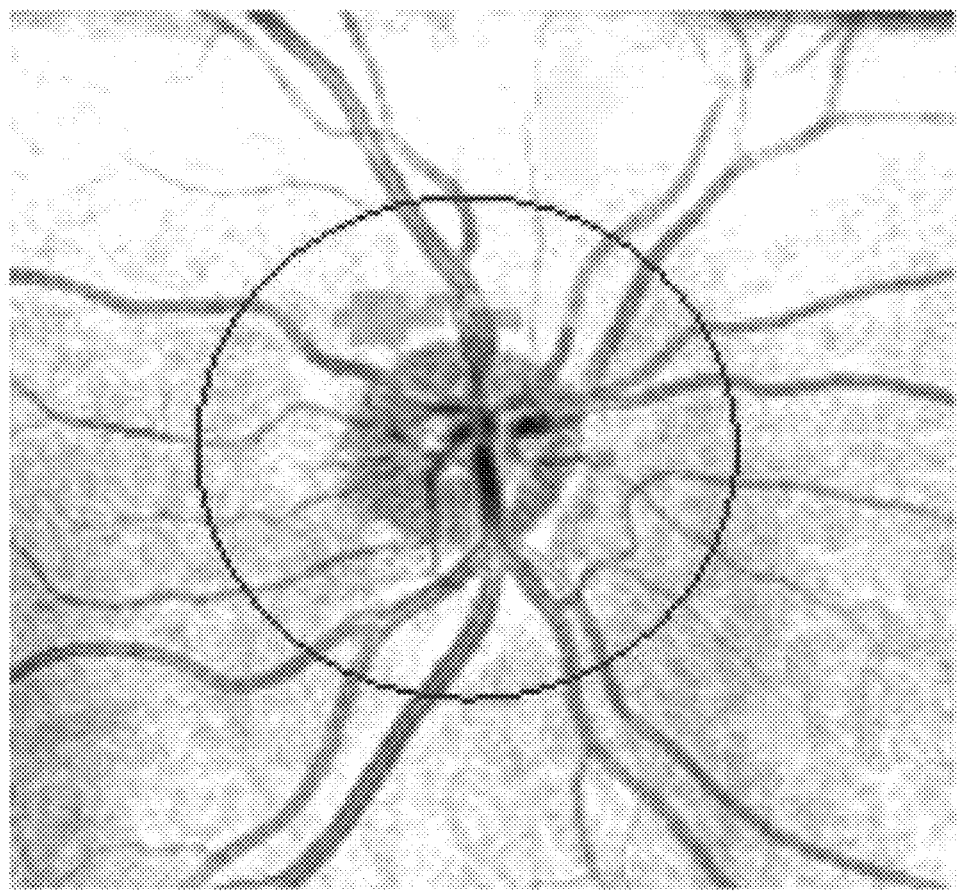
FIG. 2 is an image of an example of optic nerve.

Referring to FIG. 2, the retinal ganglion cell axon forming the RNFL passes through the optic nerve head to form the optic nerve. The optic nerve is divided at the optic nerve head into fibers responsible for superior and inferior region visual fields, and divided at the optic chiasm region into fibers responsible temporal and nasal visual fields, which are distributed and connected to the areas responsible for vision.

The optic nerve fibers form the optic nerves at the optic nerve head where the optic nerves are divided into bundles according to a unique pattern. Accordingly, the optic nerve fibers in a normal person are divided into bundles and exit to the optic nerve according to a predetermined rule, and in one embodiment of the present invention, the presence of pathological factor can be determined based on this by inspecting the pattern of the RNFL acquired by circular scanning along the optic nerve margin in the proximity of the optic nerve head.

Figure 3:
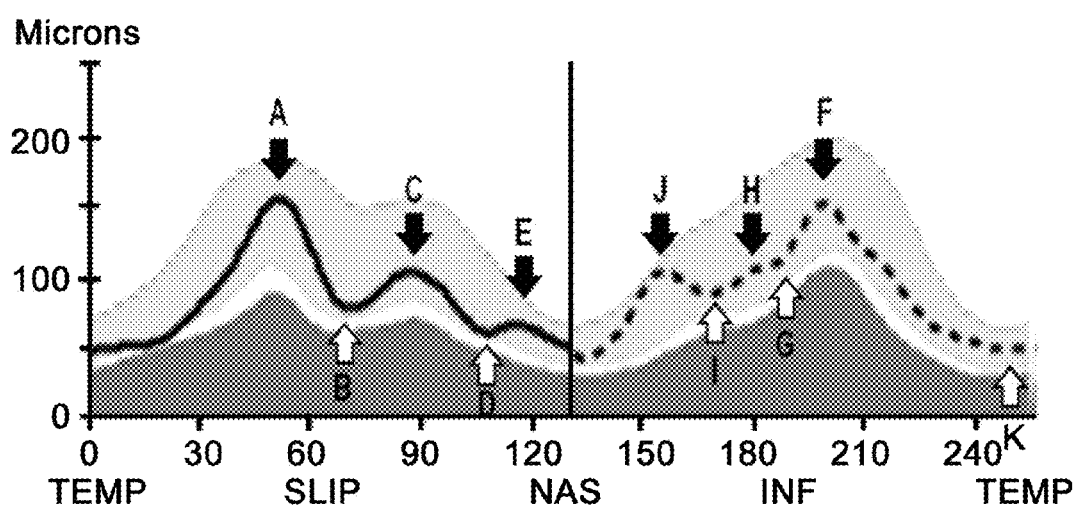
FIG. 3 is a graphical representation of an exemplary pattern of retinal nerve fiber layer (RNFL)

The scanning unit 110 scans along the optic nerve margin in the proximity of the optic nerve head. The scanning unit 110 may desirably scan along the optic nerve margin circularly in the proximity of the optic nerve head. As a result of the circular scanning along the optic nerve margin, the RNFL with varying thickness (i.e., thicker layer, thinner layer) as shown in FIG. 3 is acquired, based on which the statistically-meaningful correlation between thicker and thinner layers in normal human eye is explained and a plausible regression equation is computed therefrom. In FIG. 3, 'TEMP' denotes temporal, SUP' is superior, NAS is nasal, and INF is inferior. Additionally, dark arrows A, C, E, F, H and J indicate peaks, while blank arrows B, D, G, I and K indicate trough. The 'peak' herein refers to a location where the RNFL thickness is higher than before or after, and 'trough' herein refers to a location where the RNFL thickness is lower than before or after. The region spanning from 0 to 127 indicates superior region, and the region spanning from 128 to 255 indicates inferior region. Accordingly, arrow A corresponds to the first peak of the superior region, arrow B is the first trough of the superior region, C is the second peak of the superior region, D is the second trough of the superior region, and E is the third peak of the superior region. Also, arrow F is the first peak of the inferior region, G is the second trough of the inferior region, H is the second peak of the inferior region, I is the second trough of the inferior region, J is the third peak of the inferior region, and K is the peak of the temporal region.

In the manner explained above, the pattern analyzing unit 120 analyzes the pattern of the RNFL scanned by the scanning unit 110. In such a situation, the pattern analyzing unit 120 may compute a regression equation based on the pattern of the RNFL scanned by the scanning unit 110.

For example, the following regression equation may be computed based on the locations and thicknesses of the first and second peaks of the superior region of the optic nerve head, and the locations and thicknesses of the troughs appearing between the first and second peaks:

$$0.867 \times \text{Point of Sup. 1st peak} + 0.308 \times \text{RNFL thickness of Sup. 1st peak} - 1.763 \times \text{Point of Sup. 2nd peak} + 0.513 \times \text{RNFL thickness of Sup. 2nd Peak} + 0.905 \times \text{Point of the trough between sup. 1st and 2nd peak} - \text{RNFL thickness of the trough between sup. 1st and 2nd peak} = C1 \quad \text{[Equation 1]}$$

Additionally, the following regression equation may be computed based on the locations and thicknesses of the second and third peaks of the superior region of the optic nerve head, and the locations and thicknesses of the troughs appearing between the second and third peaks:

$$-1.248 \times \text{Point of Sup. 3rd peak} + 0.922 \times \text{RNFL thickness of Sup. 3rd Peak} + 1.238 \times \text{Point of the tough between sup. 2nd and 3rd peak} - \text{RNFL thickness of the tough between sup. 2nd and 3rd peak} = C2 \quad \text{[Equation 2]}$$

Additionally, the following regression equation may be computed based on the locations and thicknesses of the first and second peaks of the inferior region of the optic nerve head, and the locations and thicknesses of the trough appearing between the first and second peaks.

$$-0.505 \times \text{Point of Inf. 1st peak} + 0.103 \times \text{RNFL thickness of Inf. 1st peak} + 1.961 \times \text{Point of Sup. 2nd peak} + 0.758 \times \text{RNFL thickness of Inf. 2nd Peak} - 1.679 \times \text{Point of the trough between inf. 1st and 2nd peak} - \text{RNFL thickness of the trough between sup. 1st and 2nd peak} = C3 \quad \text{[Equation 3]}$$

Additionally, the following regression equation may be computed based on the locations and thicknesses of the second and third peaks of the inferior region of the optic nerve head, and the locations and thicknesses of the troughs appearing between the second and third peaks:

$$0.041 \times \text{RNFL thickness of Inf. 1st peak} + 1.127 \times \text{Point of Inf. 3rd peak} + 0.869 \times \text{RNFL thickness of Inf. 3rd Peak} - 1.084 \times \text{Point of the trough between inf. 2nd and 3rd peak} - \text{RNFL thickness of the trough between inf. 2nd and 3rd peak} = C4 \quad \text{[Equation 4]}$$

Additionally, the following regression equation may be computed based on the locations and thicknesses of the first peaks of the superior and inferior regions of the optic nerve head, and the locations and thicknesses of the troughs appearing between the first peaks:

$$-0.380 \times \text{Point of Sup. 1st peak} + 0.076 \times \text{RNFL thickness of Sup. 1st peak} + 0.266 \times \text{Point of Inf. 1st Peak} + 0.071 \times \text{RNFL thickness of the Inf. 1st Peak} = C5 \quad \text{[Equation 5]}$$

The disease determining unit 130 determines the presence of disease based on the pattern of the FNFL analyzed by the pattern analyzing unit 110. Each of C1, C2, C3, C4, and C5 of Equations 1 to 5 corresponds to a difference between an estimate and an actual measurement, and accordingly, these values fall under a normal range with respect to a healthy person, but exceeds the normal range with respect to a patient with glaucoma, or if the inspection is flawed. Based on the above phenomenon, the disease determining unit 130 determines the presence of a disease, if the difference between the estimate and the actual measurement based on the computed regression equation exceeds the predetermined range.

The respective coefficients of regression equations 1 to 5 were obtained statistically during the process of converting the correlation between the thicker areas (peaks) and the thinner areas (troughs) based on the distribution of RNFL thicknesses of 244 normal adults (i.e., adults without ophthalmological or neurological abnormalities) who aged from 19 to 20s.

Figure 4:
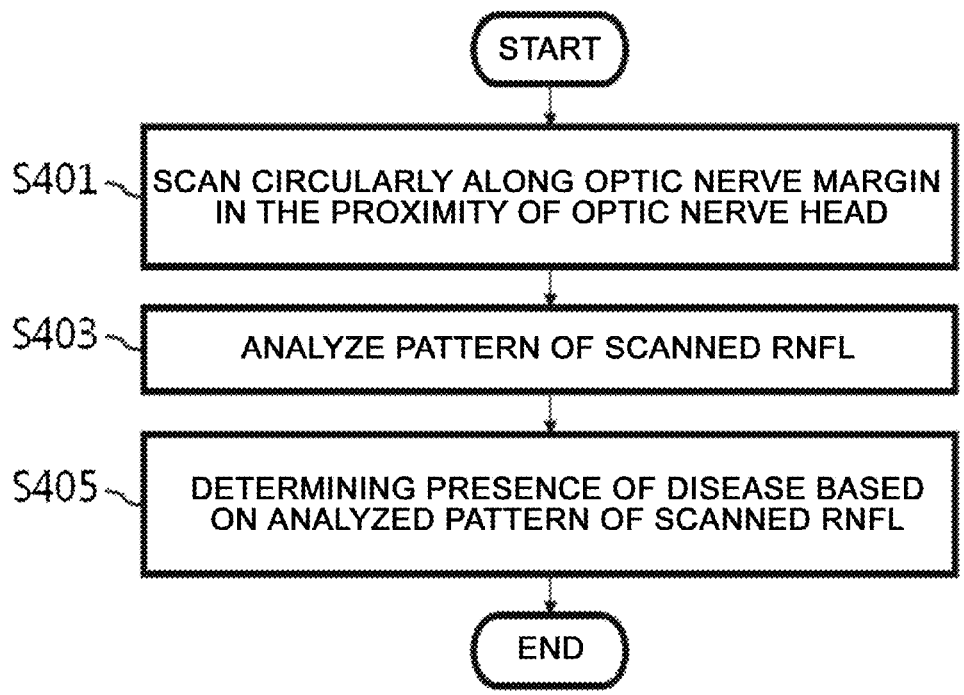
FIG. 4 is a flowchart of a method for diagnosing optic neuropathic diseases with the apparatus of FIG. 1.

FIG. 4 is a flowchart of a method for diagnosing optic neuropathic diseases with the apparatus of FIG. 1.

At S401, the scanning unit 110 scans along the optic nerve margin in the proximity of the optic nerve head. The scanning unit 110 may desirably scan along the optic nerve margin circularly in the proximity of the optic nerve head.

At S403, the pattern analyzing unit 120 analyzes the pattern of the RNFL scanned by the scanning unit 110. In this situation, the pattern analyzing unit 120 may compute a regression equation based on the pattern of the RNFL scanned by the scanning unit 110.

For example, as in the case of above Equation 1, the regression equation may be computed based on the locations and thicknesses of the first and second peaks of the superior region of the optic nerve head, and the locations and thicknesses of the troughs appearing between the first and second peaks.

Additionally, as in the case of above Equation 2, the regression equation may be computed based on the locations and thicknesses of the second and third peaks of the superior region of the optic nerve head, and the locations and thicknesses of the troughs appearing between the second and third peaks.

Additionally, as in the case of above Equation 3, the regression equation may be computed based on the locations and thicknesses of the first and second peaks of the inferior region of the optic nerve head, and the locations and thicknesses of the trough appearing between the first and second peaks.

Additionally, as in the case of above Equation 4, the regression equation may be computed based on the locations and thicknesses of the second and third peaks of the inferior region of the optic nerve head, and the locations and thicknesses of the troughs appearing between the second and third peaks:

Additionally, as in the case of above Equation 5, the regression equation may be computed based on the locations and thicknesses of the first peaks of the superior and inferior regions of the optic nerve head, and the locations and thicknesses of the troughs appearing between the first peaks.

At S405, the disease determining unit 130 determines the presence of disease based on the pattern of the FNFL analyzed by the pattern analyzing unit 110. Each of C1, C2, C3, C4, and C5 of Equations 1 to 5 corresponds to a difference between an estimate and an actual measurement, and accordingly, while these values fall under a normal range with respect to a healthy person, the values exceed the normal range with respect to a patient with glaucoma, or if the inspection is flawed. Based on the above phenomenon, the disease determining unit 130 determines the presence of a disease, if the difference between the estimate and the actual measurement based on the computed regression equation exceeds the predetermined range.

In the above description, where all the elements of the embodiment are connected integrally, or connected and operated integrally, the invention is not limited to such embodiment only. Accordingly, within the scope of object of the present invention, the constituent elements may be selectively connected and operated with one or more thereof. Furthermore, while all the constituent elements are implementable as a single individual hardware, a part or entirety of each constituent element may also be selectively combined to be implemented as a computer program having a program module to carry out a part or entirety of the combined function of one or a plurality of hardware. Furthermore, the embodiments of the present invention may be achieved in a manner in which said computer program is stored to a computer-readable media such as USB memory, CD disc, or flash memory which is readable by a computer, to be read and executed. The storage media of the computer program may include a magnetic recording medium, an optical recording medium, or a carrier wave medium.

Furthermore, unless defined otherwise in the detailed description, all the terms containing technical or scientific terms carry the same meaning as understood generally by those skilled in the art where the present invention pertains. The generally-used terms according to the definitions on the dictionary should be interpreted in line with the contextual meaning in the related technical area, and unless defined specifically in the present invention, these are not to be interpreted in an ideal or excessively-formal manner The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims, and many alternatives, modifications, and variations will be apparent to those skilled in the art.

What is claimed is:

1. A computer-implemented method for analyzing a pattern of retinal nerve fiber layer (RNFL) thickness, the method comprising:
    (a) extracting a peak value and a trough value at a given location from a two-dimensional data of RNFL thickness;
    (b) computing a difference between an estimate and an actual measurement by inputting the peak value and the trough value into a regression equation obtained statistically from a process of converting a correlation between peaks and troughs based on distributions of RNFL thicknesses of normal people; and
    (c) determining a presence or an absence of an optic neuropathic disease by comparing a range of the difference with normal peoples';
wherein the steps of the computer-implemented method are performed by one or more processors.

2. The method of claim 1, wherein the regression equation is based on locations and thicknesses of a first and second nearest peaks from superior region of optic nerve head and a trough between them.

3. The method of claim 1, wherein the regression equation is based on locations and thicknesses of a second and third nearest peaks from superior region of optic nerve head and a trough between them.

4. The method of claim 1, wherein the regression equation is based on locations and thicknesses of a first and second nearest peaks from inferior region of optic nerve head and a trough between them.

5. The method of claim 1, wherein the regression equation is based on locations and thicknesses of a second and third nearest peaks from inferior region of optic nerve head and a trough between them.

6. The method of claim 1, wherein the regression equation is based on locations and thicknesses of first nearest peak from superior and inferior regions of optic nerve head, respectively.

* * * * *